US011053270B2

United States Patent
Sensoy et al.

(10) Patent No.: US 11,053,270 B2
(45) Date of Patent: Jul. 6, 2021

(54) HETEROBIVALENT LIGANDS SUITABLE FOR USE IN THE TREATMENT OF PARKINSON'S DISEASE

(71) Applicants: T.C ISTANBUL MEDIPOL ÜNIVERSITESI, Istanbul (TR); BAHÇESEHIR ÜNIVERSITESI, Istanbul (TR)

(72) Inventors: Özge Sensoy, Istanbul (TR); Mustafa Güzel, Istanbul (TR); Bilal Ersen Kerman, Istanbul (TR); Neslihan Üstündag Okur, Istanbul (TR); Samman Mansoor, Istanbul (TR); Essam Hanashalshahaby, Istanbul (TR); Elif Keskin, Istanbul (TR); Serdar Durdagi, Istanbul (TR); Gülru Kayik, Istanbul (TR)

( * ) Notice: Subject to any disclaimer, the term of this patent is extended or adjusted under 35 U.S.C. 154(b) by 125 days.

(21) Appl. No.: 16/606,065

(22) PCT Filed: Apr. 14, 2018

(86) PCT No.: PCT/TR2018/050166
§ 371 (c)(1),
(2) Date: Oct. 17, 2019

(87) PCT Pub. No.: WO2019/004970
PCT Pub. Date: Jan. 3, 2019

(65) Prior Publication Data
US 2021/0147421 A1 May 20, 2021

(30) Foreign Application Priority Data
Apr. 18, 2017 (TR) .................................. 2017/05700

(51) Int. Cl.
| | | |
|---|---|---|
| C07H 19/16 | (2006.01) | |
| A61K 31/7076 | (2006.01) | |
| A61P 25/28 | (2006.01) | |
| A61K 45/06 | (2006.01) | |

(52) U.S. Cl.
CPC ......... *C07H 19/16* (2013.01); *A61K 31/7076* (2013.01); *A61P 25/28* (2018.01); *A61K 45/06* (2013.01)

(58) Field of Classification Search
None
See application file for complete search history.

(56) References Cited

U.S. PATENT DOCUMENTS 5,688,774 A  11/1997 Jacobson et al.

FOREIGN PATENT DOCUMENTS

WO   9425462 A1  11/1994

OTHER PUBLICATIONS

Jorg et al., "Synthesis and Pharmacological Evaluation of Dual Acting Ligands Targeting the Adenosine A2A and Dopamine D2 Receptors for the Potential Treatment of Parkinson's Disease" Journal of Medicinal Chemistry vol. 58 pp. 718-738, DOI: 10.1021/jm501254d (Year: 2015).*
Narlawar et al., "Hybrid Ortho/Allosteric Ligands for the Adenosine A1 Receptor" Journal of Medicinal Chemistry vol. 53 pp. 3028-3037, DOI: 10.1021/jm901252a (Year: 2010).*
Jacobson et al., "A Novel Pharmacological Approach to Treating Cardiac Ischemia: Binary Conjugates of A1 and A3 Adenosine Receptor Agonists" The Journal of Biological Chemistry vol. 275 No. 39 Sep. 29, pp. 30272-30279, DOI 10.1074/jbc.M001520200 (Year: 2000).*
Glennon et al., "Mesoionic Xanthine Analogues: Antagonists of Adenosine Receptors" Journal of Medicinal Chemistry vol. 27 pp. 1364-1367 (Year: 1984).*
Camaioni et al., "Adenosine Receptor Agonists: Synthesis and Biological Evaluation of the Diastereoisomers of 2-(3-Hydroxy-3-phenyl-1-propyn-1-yl) NECA" Bioorganic and Medicinal Chemistry vol. 5 No. 12 pp. 2267-2275 (Year: 1997).*
International Search Report for corresponding PCT/TR2018/050166.
Evidence for the heterotetrameric structure of the adenosine A2A-dopamine D2 receptor complex. Casadó-Anguera, V., Bonaventura, J., Moreno, E., Navarro, G., Cortés, A., Ferré, S., & Casadó, V Biochemical Society Transactions, 44 (2), 595-600, Apr. 11, 2016.
The adenosine A2A antagonistic properties of selected C8-substituted xanthines. Van der Walt, M., Terre'Blanche, G., Petzer, A., Lourens, A., & Petzer, J. Bioorganic Chemistry, 49, 49-58, Jul. 4, 2013.
Allosteric mechanisms within the adenosine A2A-dopamine D2 receptor heterotetramer. Ferré, S., Bonaventura, J., Tomasi, D., Navarro, G., Moreno, E., & Cortés, A. et al. Neuropharmacology, 104, 154-160, May 28, 2016.

* cited by examiner

*Primary Examiner* — Eric Olson

(57) ABSTRACT

Disclosed are novel drug molecules and use of the novel drug molecules in the treatment of neurodegenerative diseases, such as Parkinson's disease.

10 Claims, No Drawings

HETEROBIVALENT LIGANDS SUITABLE FOR USE IN THE TREATMENT OF PARKINSON'S DISEASE

The present invention relates to the use of novel drug molecules and, use of said novel drug molecules in the treatment of neurodegenerative diseases, such as Parkinson's disease.

STATE OF THE ART

Neurodegenerative diseases are diseases in which structures or functions of neurons are damaged. Indications of commonly seen neurodegenerative diseases such as Parkinson's, Alzheimer's, Huntington's, amyotropic lateral disease and such are usually seen as a result of neurodegenerative processes.

Parkinson's disease, which is one of the most commonly encountered neurodegenerative diseases, occurs due to destruction of cells that send dopamine to the striatum region of the brain. The basic approach to treating the disease known in the art is based on increasing dopaminergic efficacy. Currently drug treatments that are widely used are intended to: i) boost dopamine from the outside in the form of L-dopa, ii) provide signal transmission of striatal dopamine receptors by the use of dopamine agonists, and iii) prevent dopamine degradation in the cell by the use of monoamine oxidase inhibitors.

Although the dopaminergic agonists give good results in the early stages of the disease, these molecules alone are not sufficient as time progresses and require L-dopa fortification. Although L-DOPA is the most effective drug in the treatment of Parkinson's disease, the activity diminishes over time and causes motor complications such as motor fluctuations and dyskinesias. In addition, its effect on the axial motor symptoms and tremor caused by the disease is limited L-dopa and dopamine agonists target the dopamine 2 receptor (D2R) belonging to the class A of the family of G-protein-coupled receptor (GPCR). Said D2R forms a heteromer structure with Adenosine 2A (A2AR) which is another class A receptor, in post-synaptic striatal cells. Hence, when GPCR is targeted, heteromeric constructs formed by more than one receptor need to be considered. The reason for this is that; due to the allosteric interaction between the receptors forming heteromer, an effect that is much more different than the effect obtained for individual receptors takes place. For example, in the heteromeric form of A2AR and D2R, A2AR has antagonistic activity on D2R and thus diminishes D2R signaling. In this regard, when antagonists specific for A2AR are used in combination with L-dopa and other dopamine agonists, there is a potential for treating the disease. In the treatment of the disease, heteromultivalent ligands containing suitable pharmacophore groups capable of binding to the same receptors when targeting multiple receptors present in the heteromer have been shown to be more effective on receptor function than ligands containing these groups separately. For this purpose, studies have been conducted to develop heterobivalent ligands comprising the A2AR antagonist/D2R agonist and targeting the A2AR-D2R heterodimer structure, but no drug has yet been developed that can be used clinically.

A study by Bonaventura et al. in 2015 showed that D2R and A2AR do not remain heterodimers, suggesting that the two heterodimers combine to form a tetramer. In the subject construct, it has been observed that the binding of the A2AR pair agonist and antagonist on the heterotetramer results in the antagonistic effect on D2R being abolished, and that the signal transduction can be increased by antagonist binding to A2AR alone. These findings suggest that heterobivalent ligands that are composed of agonists and antagonists that target the heterotetramer structure and that are specific for A2AR are potentially more effective for treatment by reducing the side effects of L-dopa by using less amount of dopamine agonist or L-dopa.

Aim of the Invention

The inventors intended to develop novel molecules suitable for use in the treatment of Parkinson's disease. The inventors who work in this direction aim to develop therapeutic molecules having heterobivalent structure targeting the A2AR pair in the heterotetramer structure.

The inventors who have carried out studies for realizing these aims have developed molecules of the formula I.

DETAILED DESCRIPTION OF THE INVENTION

The present invention relates to molecules represented by Formula I,

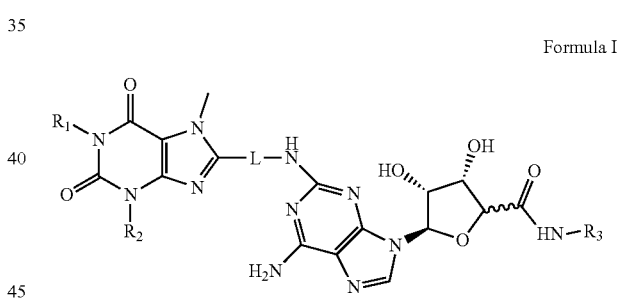

Formula I wherein;

R1, R2 and R3 are independently selected from C1-C4 alkane, alkene or alkyne,

L is a benzene ring with at least one substituent or a benzene with at least one substituent and fused to heterocyclic aromatic or non aromatic ring or a benzene with at least one substituent fused to carbocyclic ring or an aromatic heterocyclic ring with at least one substituent; wherein said ring/benzene substituents are independently selected from a group comprising C1-C5 alkane, C1-C5 alkene, C1-C5 alkyne, C1-C5 alkane comprising a carbonyl group, a C1-C5 alkene comprising a carbonyl group, a C1-C5 alkyne containing a carbonyl group, C1-C5 primary amine, C1-C5 secondary amine, C1-C5 tertiary amine, C1-C5 primary amide, C1-C5 secondary amide, C1-C5 tertiary amide, C1-C5 carboxylate, C1-C5 alkoxide, C1-C5 urea, C1-C5 sulphonamide, heterocyclopentadiene groups.

In one embodiment of the invention, the invention relates to molecules represented by Formula I,

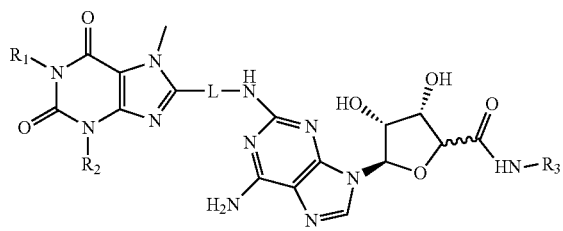

Formül I wherein;

R1, R2 and R3 are independently selected from the group comprising methyl, ethyl, propyl, isopropyl, 2-propyl, n-butyl, 1-methylpropyl, isobutyl, 1,1-dimethyl groups L group is

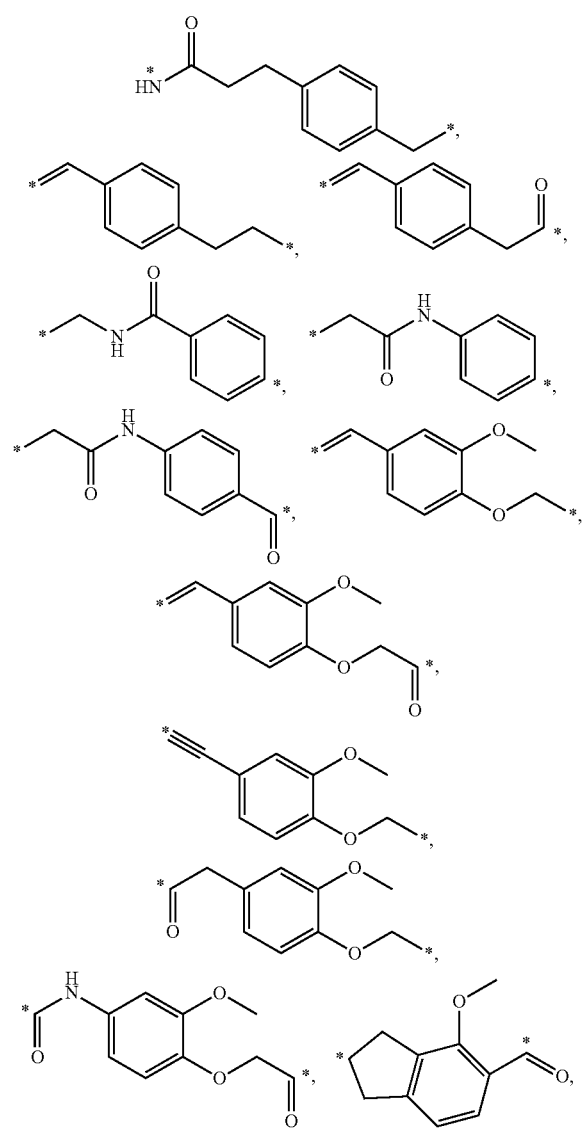

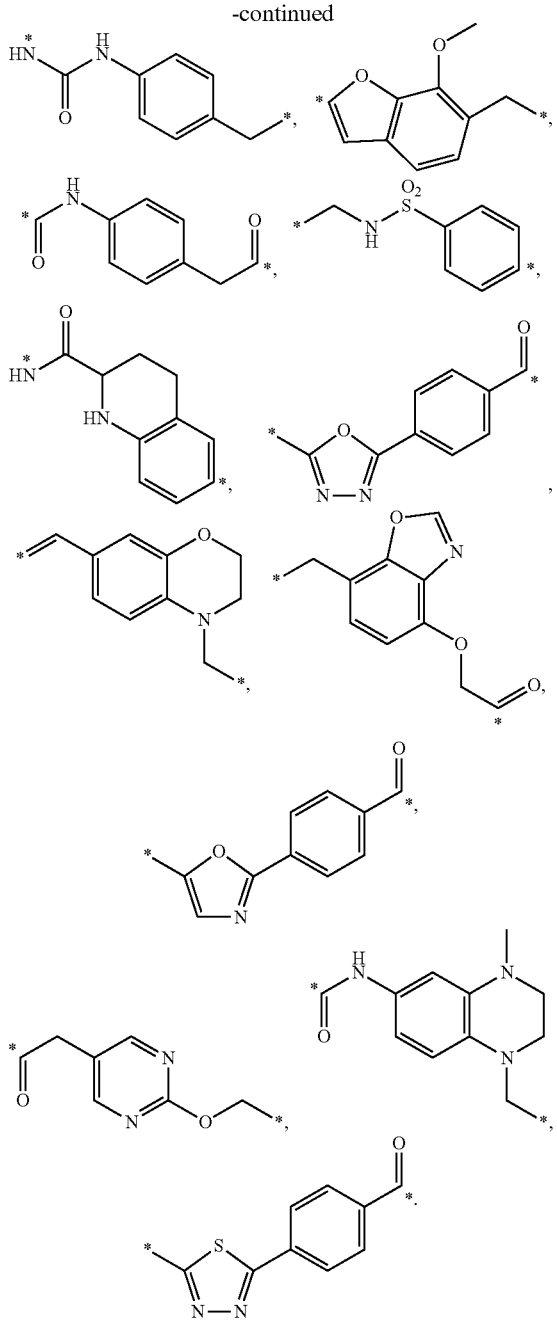

The symbol "*" shown here represents the point where the group L connects to the structure indicated by the formula I, and the "*" mark on the cyclic/ring structures indicates that the said link can be made with any atom suitable for linking on the ring.

The term "alkane"; as used in the present invention refers to straight or branched saturated hydrocarbon chains.

The term "alkene" as used in the present invention refers to straight or branched hydrocarbon chains containing at least one carbon-carbon double bond.

The term "alkyne" as used in the present invention refers to straight or branched hydrocarbon chains containing at least one carbon-carbon triple bond.

The term "carbonyl group" as used in the present invention refers to the group —C(O).

The expression "C1-C5 primary amine"; used in the context of the present invention refers to the —NH2 group attached to a hydrocarbon chain comprising 1, 2, 3, 4 or 5 carbons.

The expression "C1-C5 secondary amine"; used in the context of the present invention refers to the —NH group attached to a hydrocarbon chain comprising 1, 2, 3, 4 or 5 carbons.

The expression "C1-C5 tertiary amine" used in the context of the present invention refers to the —N group attached to a hydrocarbon chain comprising 1, 2, 3, 4 or 5 carbons.

The term "C1-C5 primary amide" used in the context of the present invention refers to the group —C(O)NH2 attached to a hydrocarbon chain comprising 1, 2, 3, 4 or 5 carbons.

The term "C1-C5 secondary amide" used in the context of the present invention refers to the group —C(O)NH attached to a hydrocarbon chain comprising 1, 2, 3, 4 or 5 carbons.

The expression "C1-C5 tertiary amide"; used in the context of the present invention refers to the group —C(O)N attached to a hydrocarbon chain comprising 1, 2, 3, 4 or 5 carbons.

The secondary and tertiary amines and amides mentioned herein may be bonded to any C1-C5 hydrocarbon chain.

The term "C1-C5 carboxylate" used in the present invention refers to the group —C(O)O.

The term "heterocyclopentadiene" used in the present invention refers to cyclopentadiene rings wherein at least one atom is a non-C atom such as S, O, N.

In one embodiment of the invention, the molecule according to the invention is shown by formula I.1.

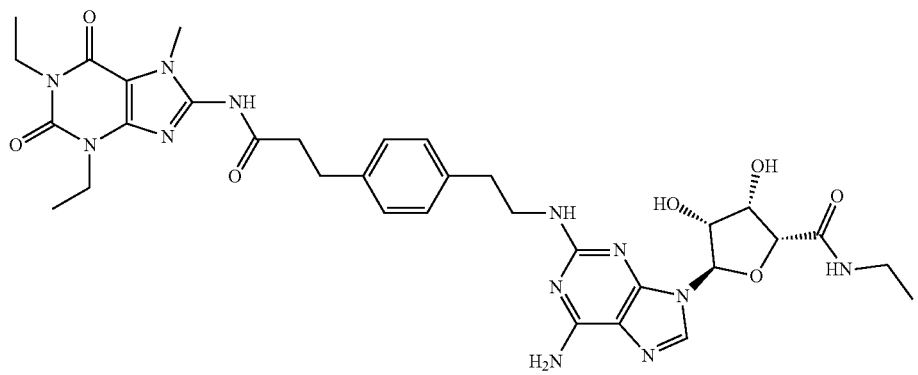

Formula I.1

In one embodiment of the invention, the molecule according to the invention is shown by formula I.2.

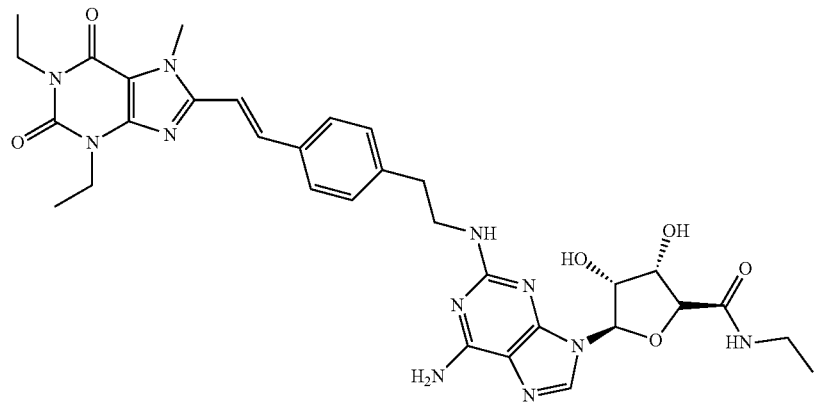

Formula I.2

In one embodiment of the invention, the molecule according to the invention is shown by formula I.3.
Formula I.3
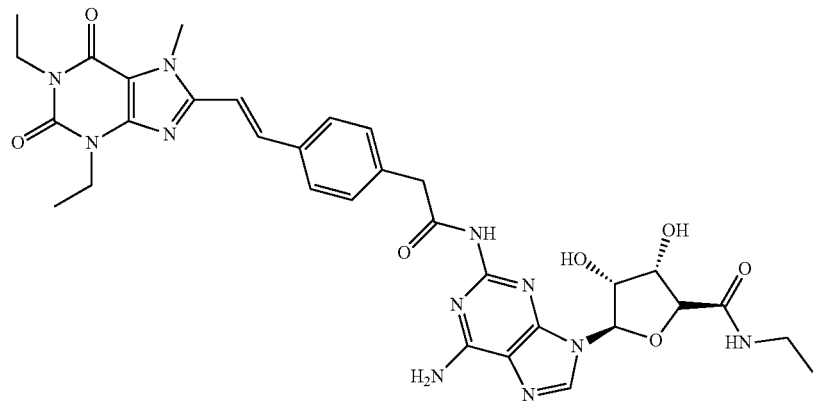
In one embodiment of the invention, the molecule according to the invention is shown by formula I.4.
Formula I.4
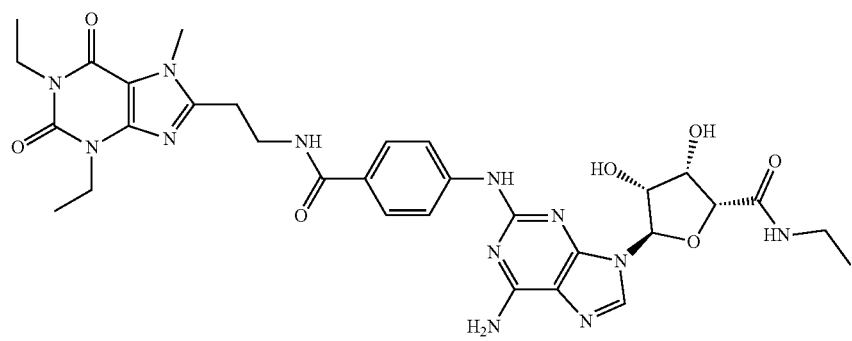
In one embodiment of the invention, the molecule according to the invention is shown by formula I.5.
Formula I.5
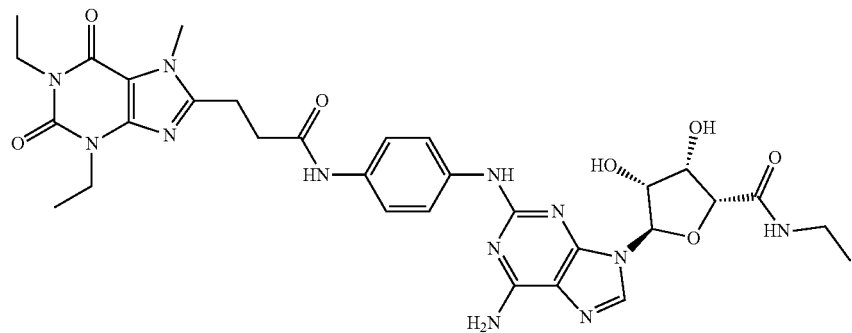

In one embodiment of the invention, the molecule according to the invention is shown by formula I.6.
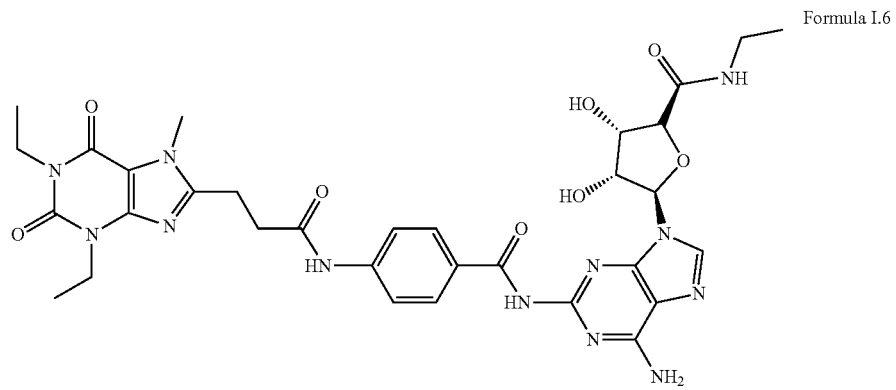
Formula I.6
In one embodiment of the invention, the molecule according to the invention is shown by formula I.7.
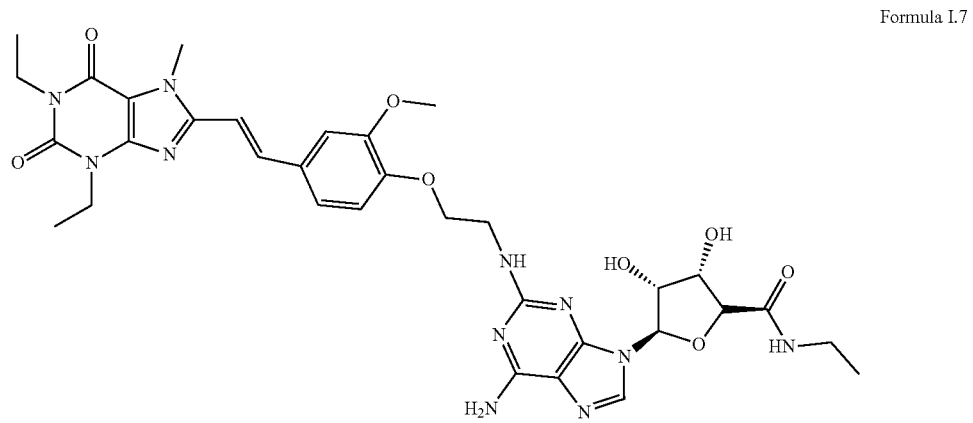
Formula I.7
In one embodiment of the invention, the molecule according to the invention is shown by formula I.8.
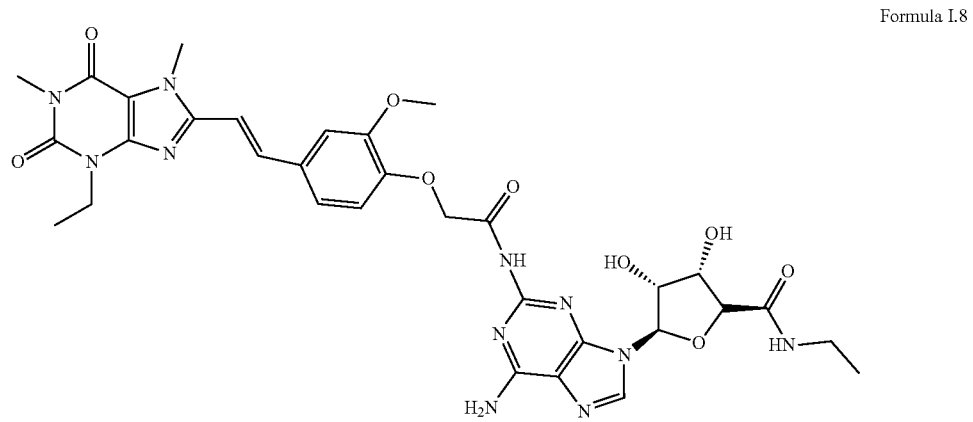
Formula I.8

In one embodiment of the invention, the molecule according to the invention is shown by formula I.9.
Formula I.9
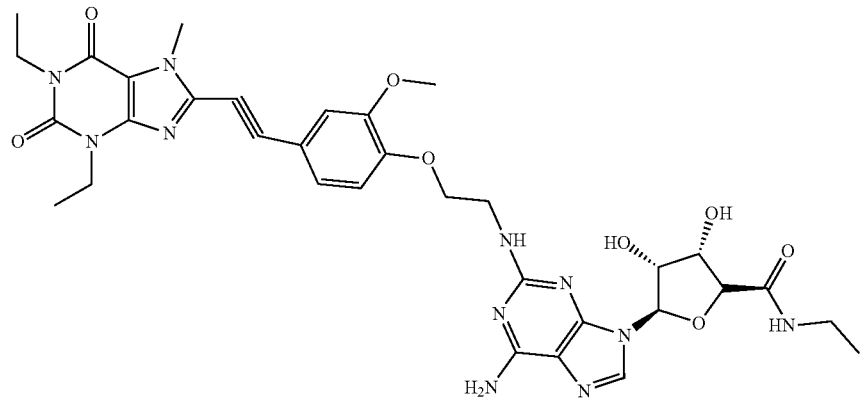
In one embodiment of the invention, the molecule according to the invention is shown by formula I.10.
Formula I.10
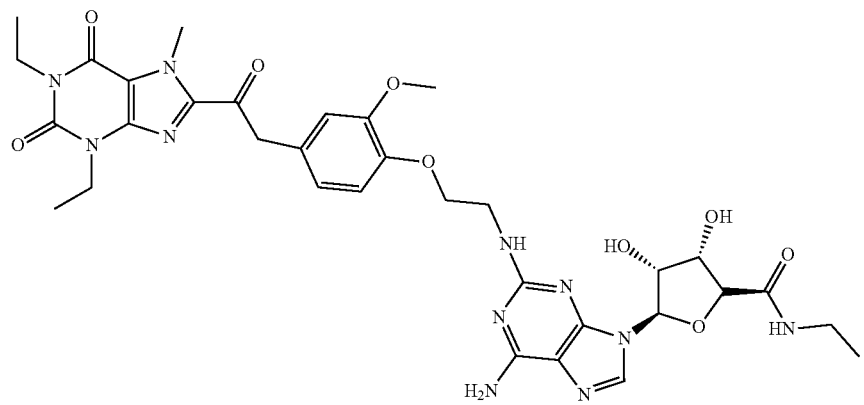
In one embodiment of the invention, the molecule according to the invention is shown by formula I.11.
Formula I.11
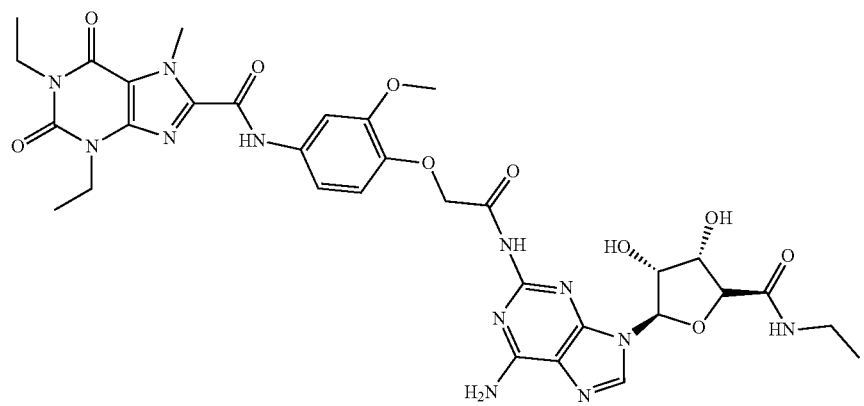

In one embodiment of the invention, the molecule according to the invention is shown by formula I.12.
Formula I.12
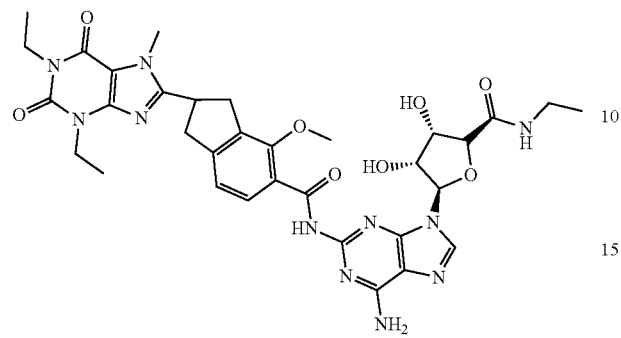
In one embodiment of the invention, the molecule according to the invention is shown by formula I.13.
Formula I.13
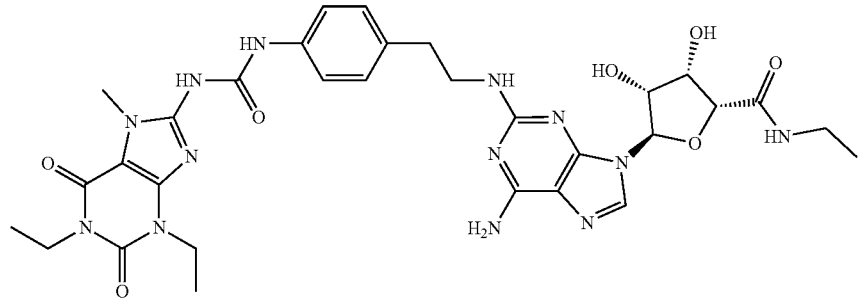
In one embodiment of the invention, the molecule according to the invention is shown by formula I.14.
Formula I.14
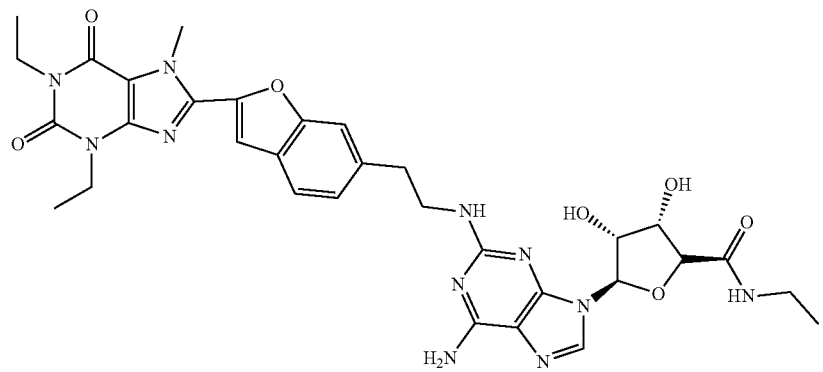

In one embodiment of the invention, the molecule according to the invention is shown by formula I.15.
Formula I.15
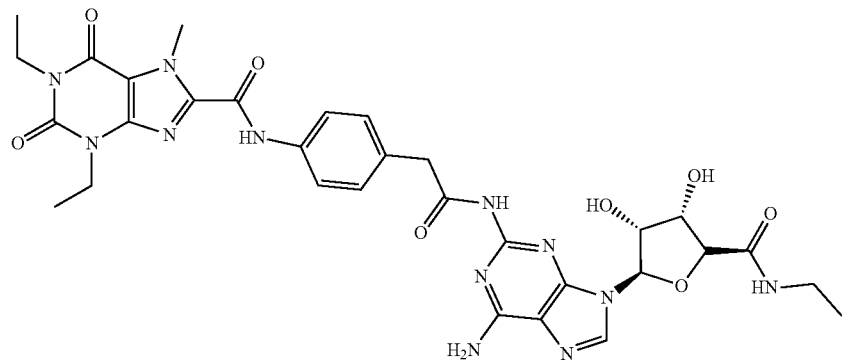
In one embodiment of the invention, the molecule according to the invention is shown by formula I.16.
Formula I.16
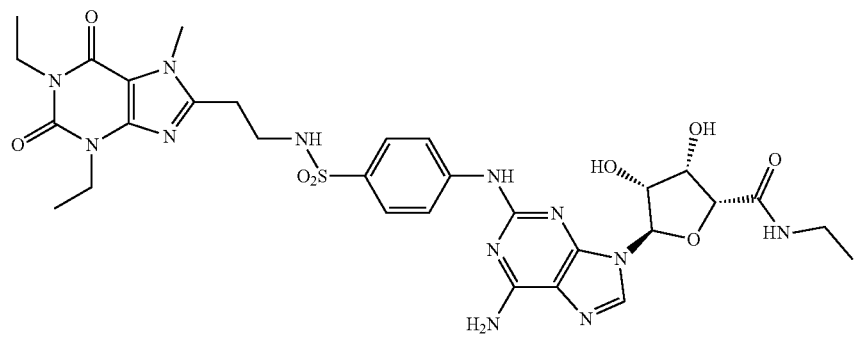
In one embodiment of the invention, the molecule according to the invention is shown by formula I.17.
Formula I.17
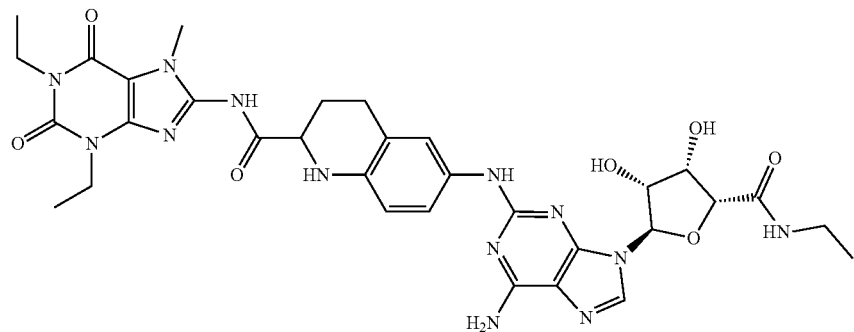

In one embodiment of the invention, the molecule according to the invention is shown by formula I.18.
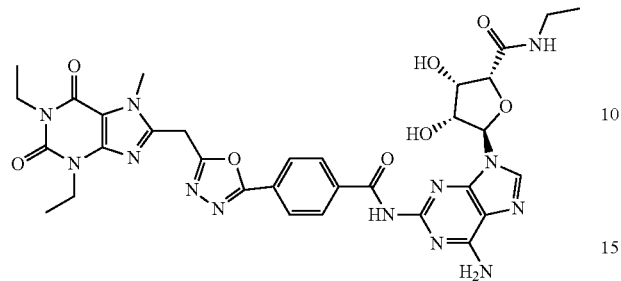
Formula I.18
In one embodiment of the invention, the molecule according to the invention is shown by formula I.19.
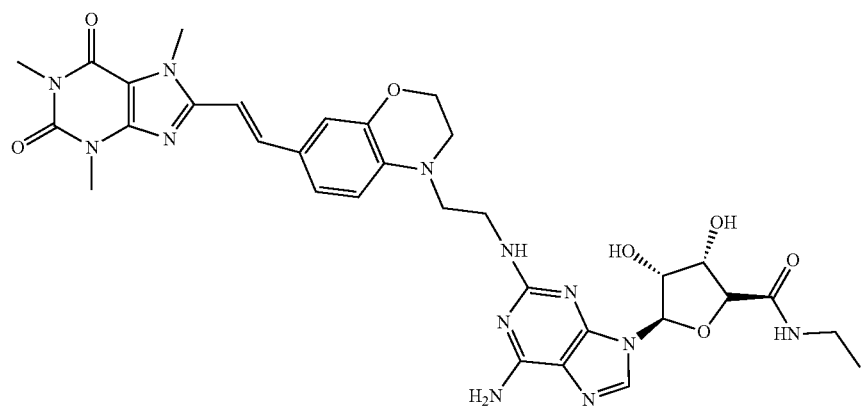
Formula I.19
In one embodiment of the invention, the molecule according to the invention is shown by formula I.20.
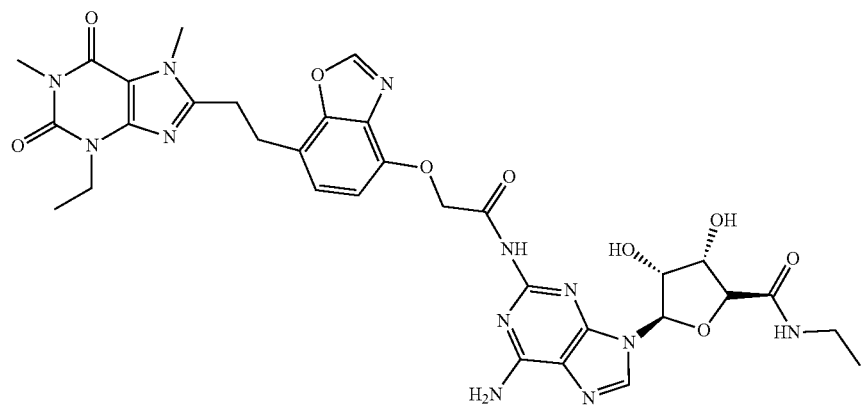
Formula I.20

In one embodiment of the invention, the molecule according to the invention is shown by formula I.21.
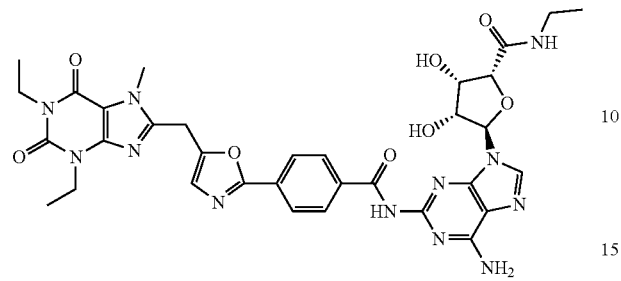
Formula I.21
In one embodiment of the invention, the molecule according to the invention is shown by formula I.22.
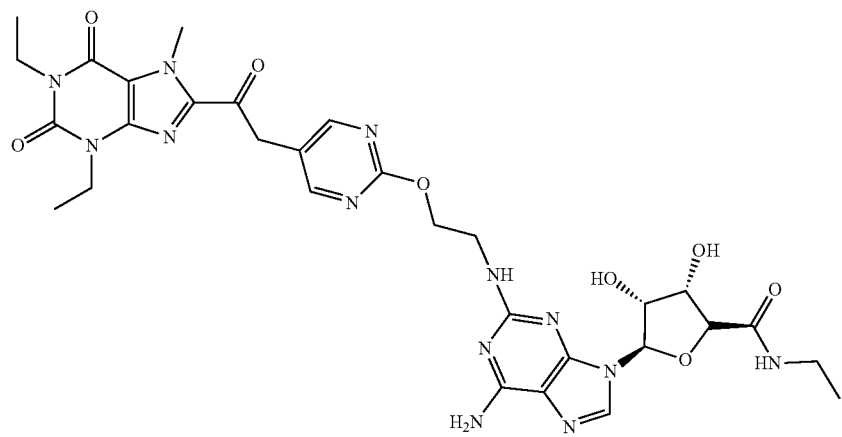
Formula I.22
In one embodiment of the invention, the molecule according to the invention is shown by formula I.23.
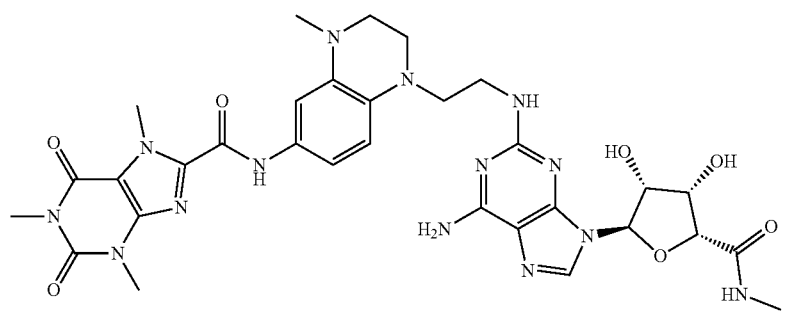
Formula I.23

In one embodiment of the invention, the molecule according to the invention is shown by formula I.24.

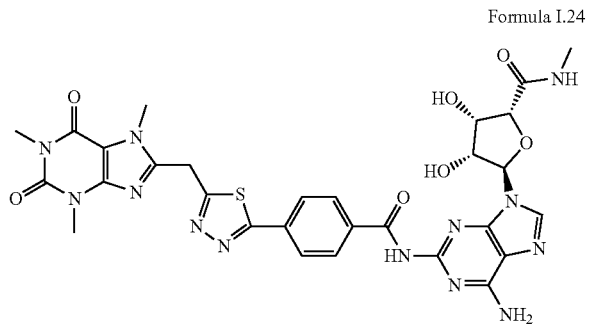

Formula I.24

The molecules of formulas I.1-I.24 whose chemical structures are given above are intended to illustrate the invention and as such the scope of the invention are not limited with these structures.

In another aspect, the present invention relates to pharmaceutically acceptable derivatives of the molecules shown with formula I.

As used herein, the term "pharmaceutically acceptable derivatives" refers to various salts, esters, polymorphs and structures which can be obtained as a result of any modification that can be made to facilitate/improve the use and/or its efficiency and/or to provide ease of formulating The Formula I molecules according to the invention can be prepared and purified using methods known in the art.

In another aspect, the invention discloses the use of the compounds of Formula I as medicaments.

In one aspect, the present invention relates to the use of the molecules of Formula I according to the invention in the treatment of neoplastic diseases.

As used herein, the term "neurodegenerative diseases"; refers to diseases characterized by the progressive deterioration of neuronal structures or functions.

The neurodegenerative diseases mentioned herein can be Parkinson's disease, Huntington's disease, Alzheimer's disease, amyotrophic lateral sclerosis (ALS), primary progressive aphasia, progressive supranuclear palsy diseases.

In a preferred embodiment of the invention, the molecules of formula I are used in the treatment of Parkinson's disease.

The invention also relates to a pharmaceutical composition comprising as active ingredient the compounds shown with formula I according to the present invention.

Said pharmaceutical compositions may comprise at least one further active ingredient in addition to the compounds represented by Formula I.

In another embodiment of the present invention, compounds of the formula I according to the present invention can be used in combination with active pharmaceutical ingredients which are known per se for the treatment of Parkinson's disease, Huntington's disease, Alzheimer's disease, amyotrophic lateral sclerosis (ALS), primary progressive aphasia or progressive supranuclear pulsatile diseases or in the treatment of symptoms known to be caused by these diseases. Said combinations can be binary or ternary combinations as well. The second active ingredient that can be formulated together with the compounds represented by formula I, or can be formulated separately from the compounds according to formula I and sold in packages suitable for combined use.

In a preferred embodiment of the invention, the compounds which can be used in combination with the compounds represented by formula I are selected from a group comprising acetylcholinesterase inhibitors, N-methyl-D-aspartate (NMDA) receptor antagonists, dopamine derivatives, anticholinergics, MAO-B inhibitors, anticonvulsants, antipsychotic agents, antidepressants.

The acetylcholinesterase inhibitors disclosed herein can be selected from a group comprising donepezil, rivastigmine and galantamine, or a pharmaceutically acceptable derivative thereof.

The NMDA receptor antagonist disclosed here is memantine

The dopaminergic derivatives disclosed herein are selected from a group comprising levodopa and/or carbidopa, or a pharmaceutically acceptable derivative thereof.

The dopamine agonists disclosed herein are selected from a group comprising pramipexole, ropinirole, rotigotine, bromocriptine, or a pharmaceutically acceptable derivative thereof.

The anticholinergics disclosed herein are selected from a group comprising trihexiphenidyl, benztropine mesylate, procyclidine or a pharmaceutically acceptable derivative thereof.

The MAO-B inhibitors disclosed herein are selected from a group comprising selegiline and rasagiline, or a pharmaceutically acceptable derivative thereof.

The COMT inhibitors disclosed herein are selected from a group comprising intecapone and tolcapone or a pharmaceutically acceptable derivative thereof.

The monaminase inhibitor disclosed herein is tetrabenazine.

The anticonvulsant disclosed herein is selected from a group comprising valproic acid, clonazepam, or a pharmaceutically acceptable derivative thereof.

The antipsychotic agents disclosed herein are selected from a group comprising risperidone, haloperidol, or a pharmaceutically acceptable derivative thereof.

The antidepressant disclosed herein is selected from a group comprising paroxetine or a pharmaceutically acceptable derivative thereof.

In another embodiment of the invention, at least one further active ingredient may be formulated together with or separately from the compounds of formula I according to the invention, and said at least one further active ingredient may be in the same or different dosage form as the compounds of formula I.

If at least one other active ingredient mentioned above is used in combination with the compounds of formula I according to the invention, the other active ingredients may be administered simultaneously, sequentially or at different times with the compounds of formula I.

The formulations according to the invention may contain at least one excipient in addition to the active substances indicated by formula I.

The dosage range in which the active compounds of the formula I according to the invention that can be used is determined according to the needs of the patient, the stage of the disease and the agent to be used.

The invention claimed is:

1. The molecules shown with Formula I wherein

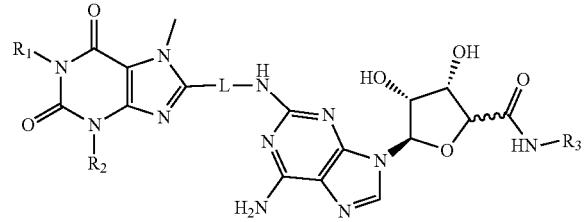

Formula I

R1, R2 and R3 are independently selected from C1-C4 alkane, alkene or alkyne,

L is a benzene ring with at least one substituent or a benzene with at least one substituent and fused to heterocyclic aromatic or non aromatic ring or a benzene with at least one substituent fused to carbocyclic ring or an aromatic heterocyclic ring with at least one substituent; wherein said ring/benzene substituents are independently selected from a group comprising C1-C5 alkane, C1-C5 alkene, C1-C5 alkyne, C1-C5 alkane comprising a carbonyl group, a C1-C5 alkene comprising a carbonyl group, a C1-C5 alkyne containing a carbonyl group, C1-C5 primary amine, C1-C5 secondary amine, C1-C5 tertiary amine, C1-C5 primary amide, C1-C5 secondary amide, C1-C5 tertiary amide, C1-C5 carboxylate, C1-C5 alkoxide, C1-C5 urea, C1-C5 sulphonamide, heterocyclopentadiene groups.

2. The molecules shown with Formula I wherein

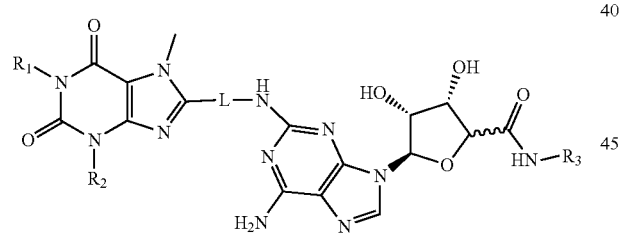

Formula I

R1, R2 and R3 are independently selected from the group comprising methyl, ethyl, propyl, isopropyl, 2-propyl, n-butyl, 1-methylpropyl, isobutyl, 1,1-dimethyl groups L group is

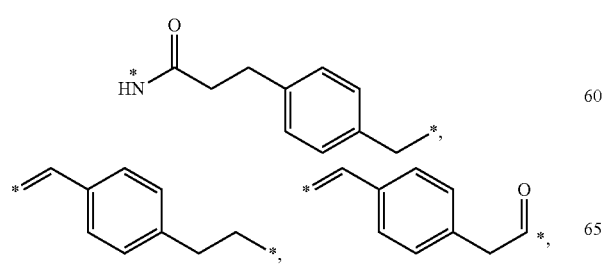

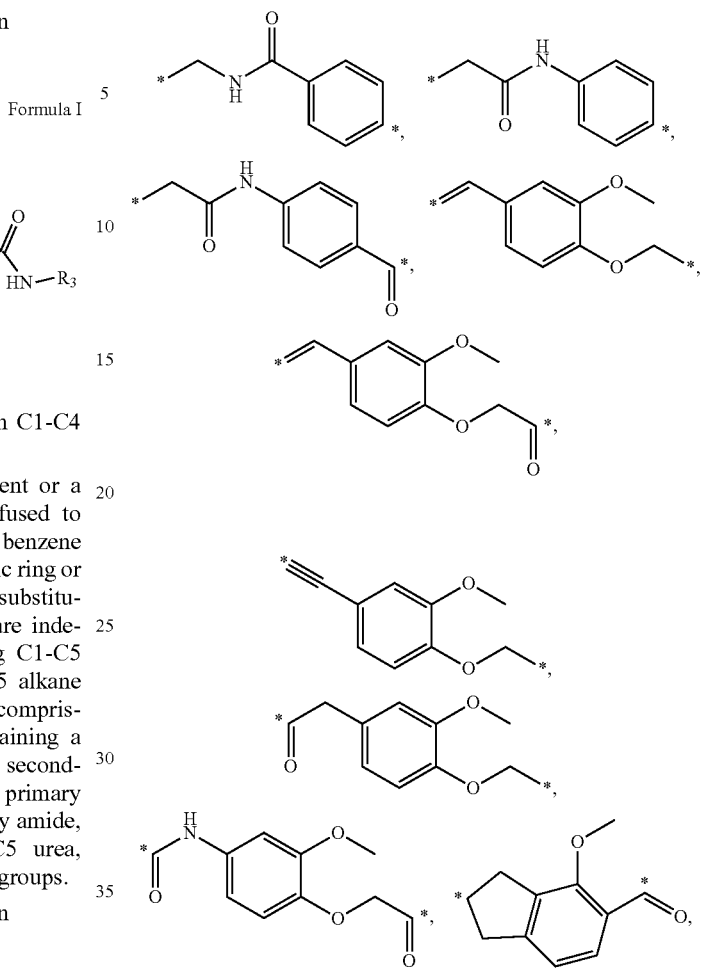

-continued
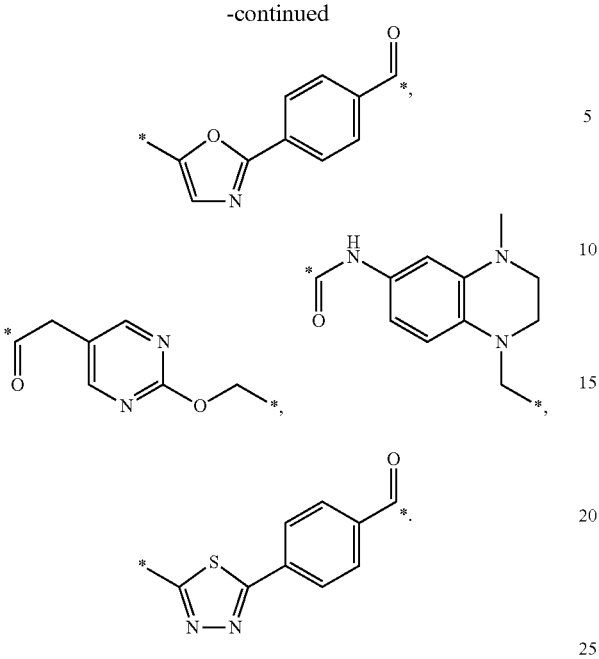
3. A molecule according to claim 1, wherein the formula is selected from a group consisting of:
formula I.1,
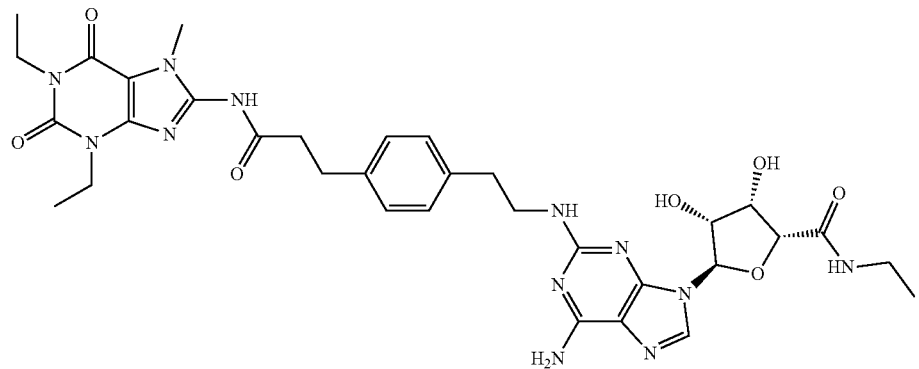
Formula I.1
formula I.2,
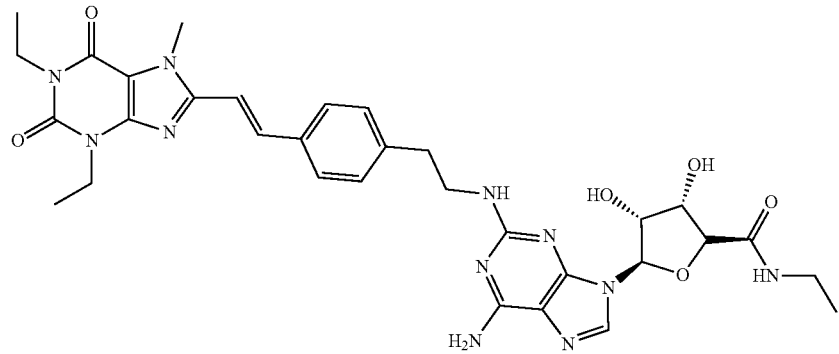
Formula I.2 formula I.3,
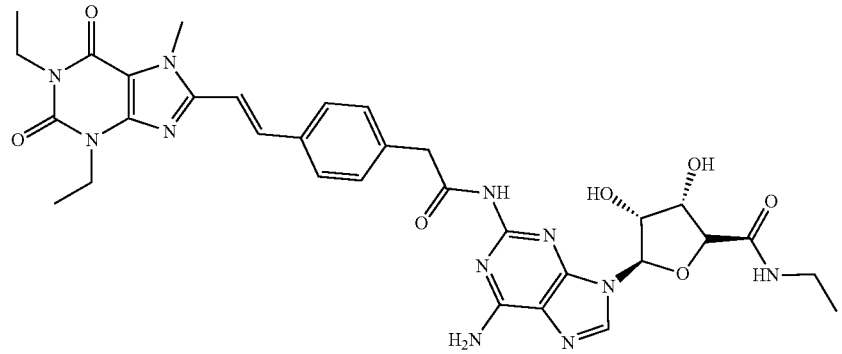
Formula I.3
formula I.4,
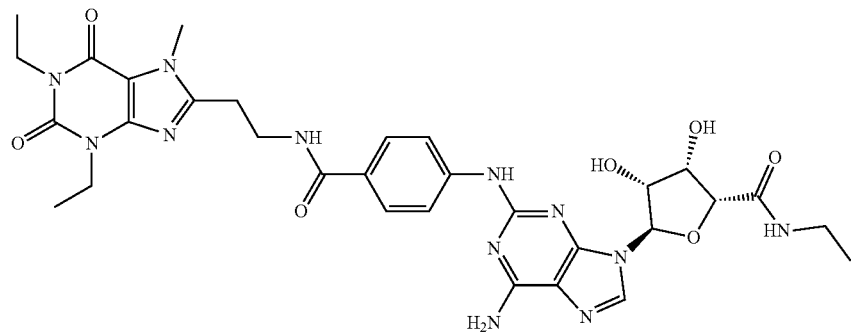
Formula I.4
formula I.5,
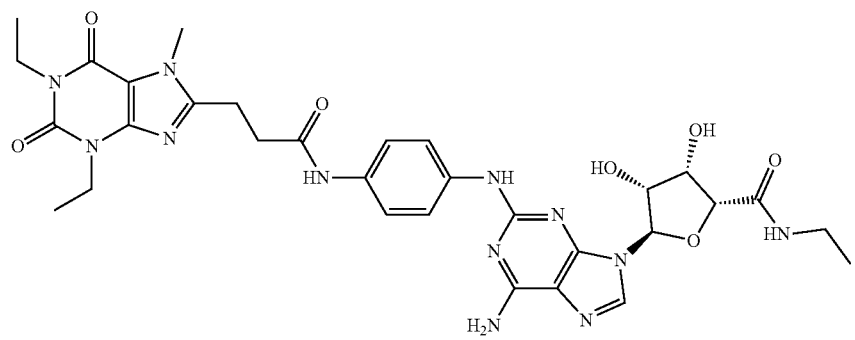
Formula I.5 formula I.6,
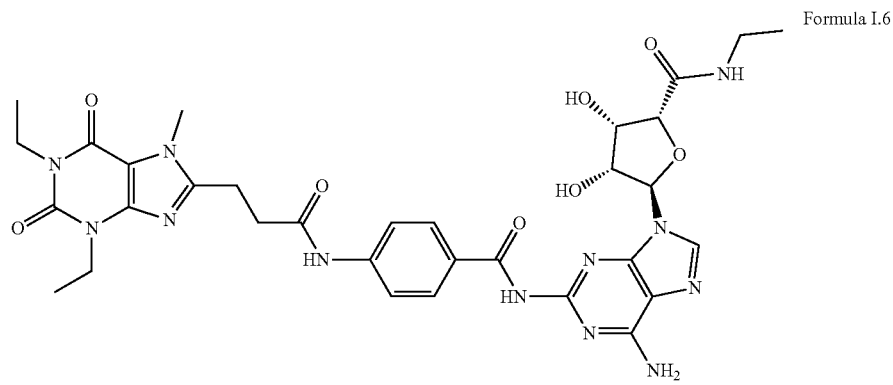 [SMILES: CCNC(=O)[C@@H]1O[C@@H](n2cnc3c(N)nc(NC(=O)c4ccc(NC(=O)CCc5nc6c(c(=O)n(CC)c(=O)n6CC)n5C)cc4)nc32)[C@H](O)[C@@H]1O]
formula I.7,
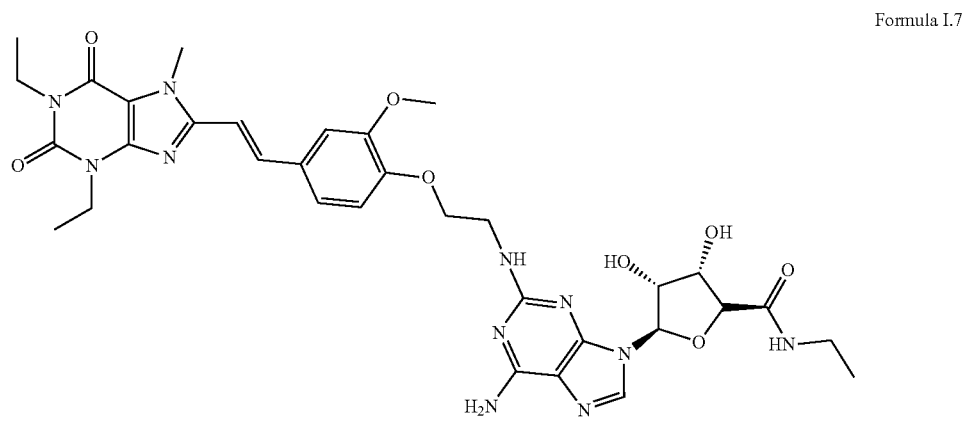
formula I.8,
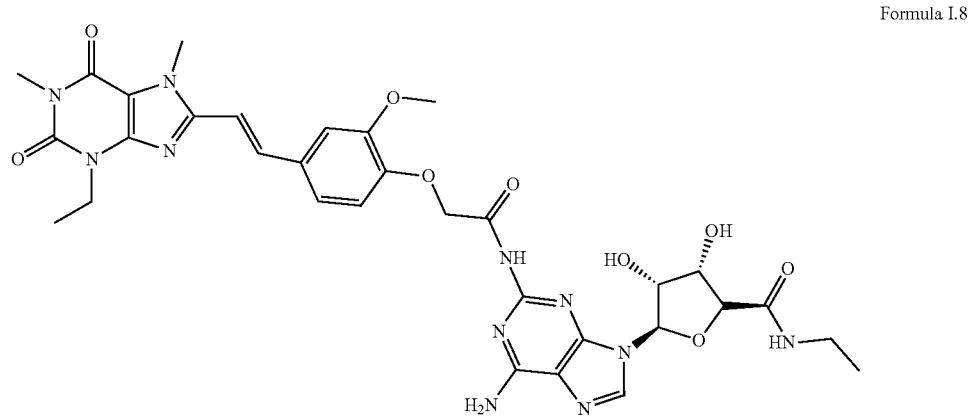

formula I.9,
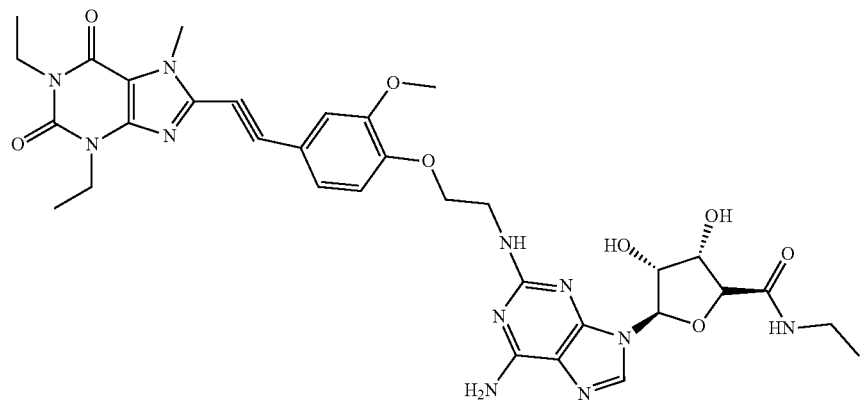
Formula I.9
formula I.10,
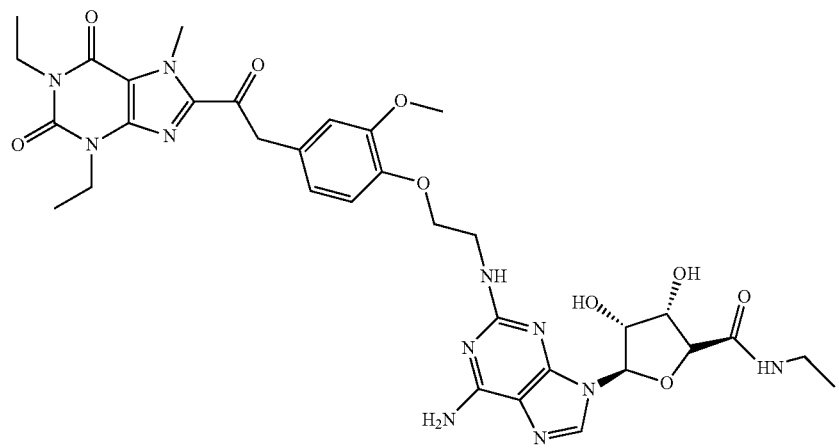
Formula I.10
formula I.11,
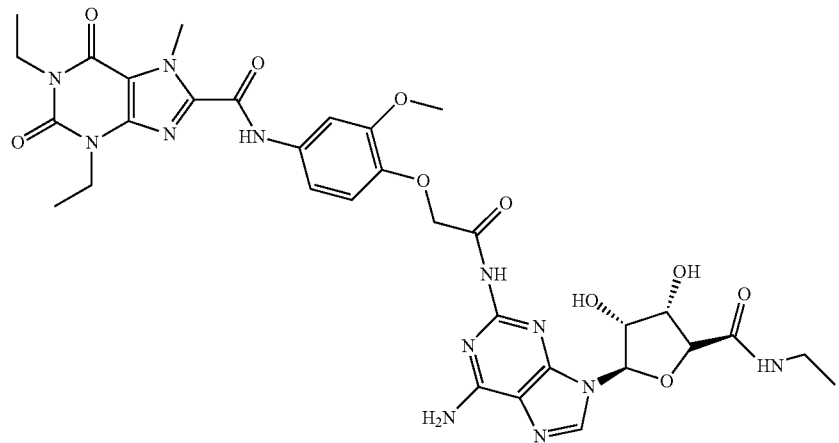
Formula I.11 formula I.12,
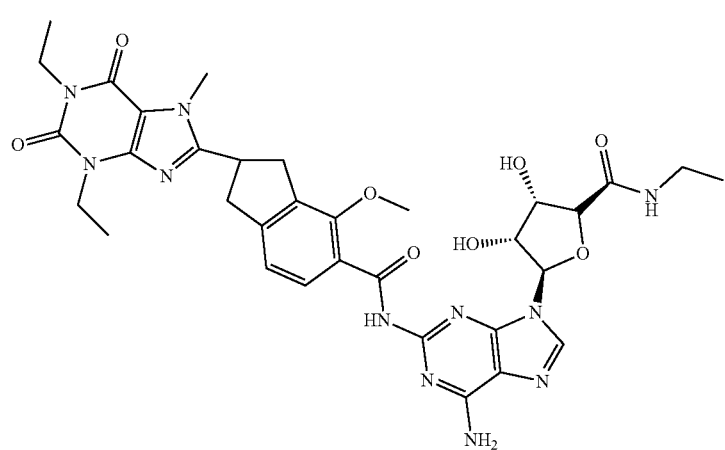
formula I.13,
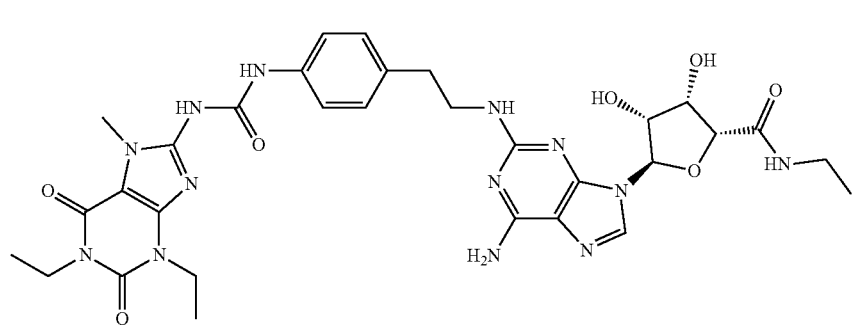
formula I.14,
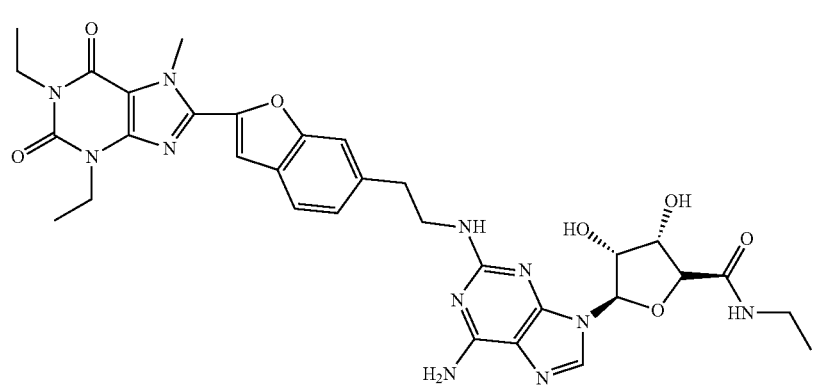

formula I.15,
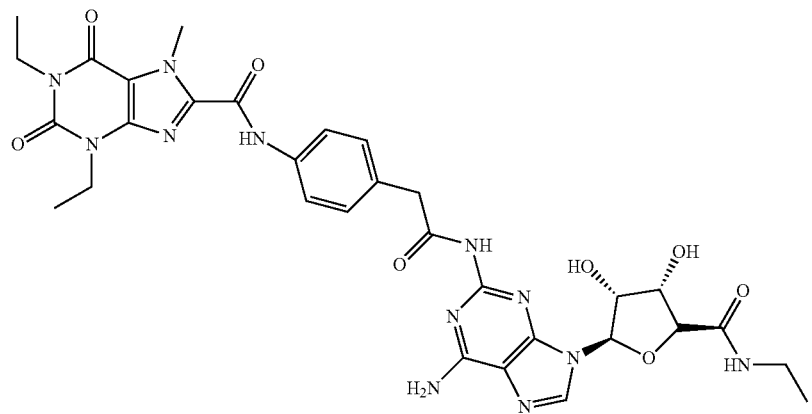
Formula I.15
formula I.16,
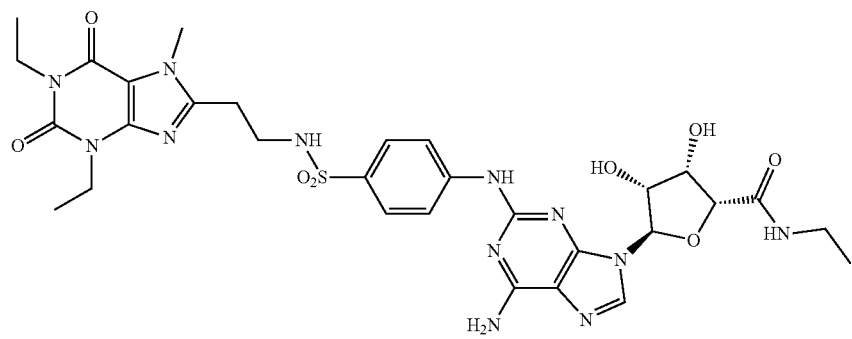
Formula I.16
formula I.17,
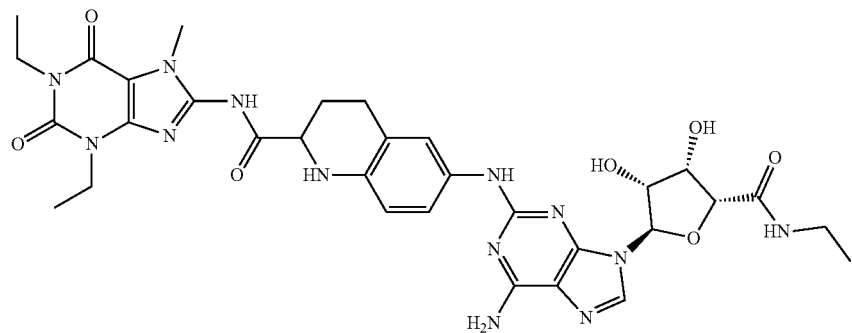
Formula I.17 formula I.18,
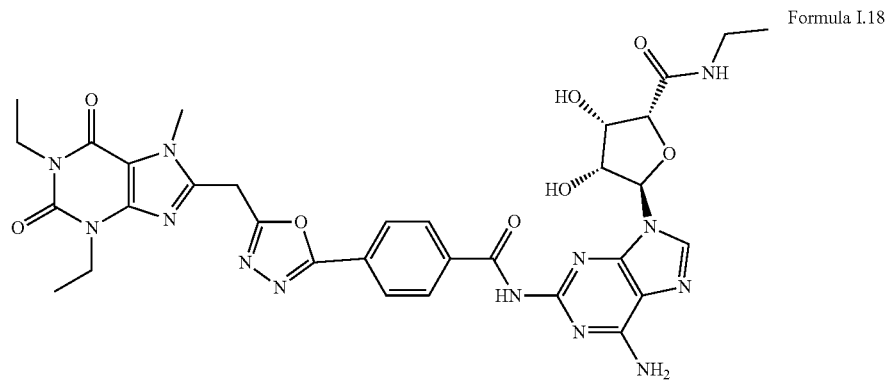
formula I.19,
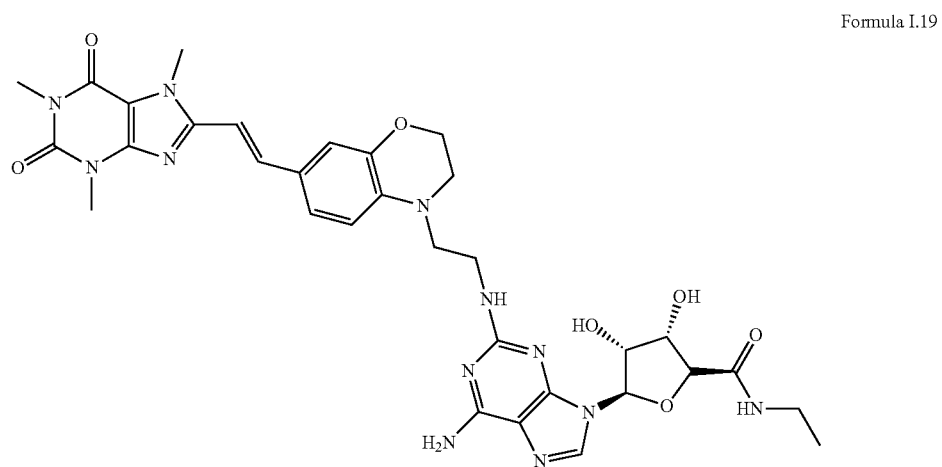
formula I.20,
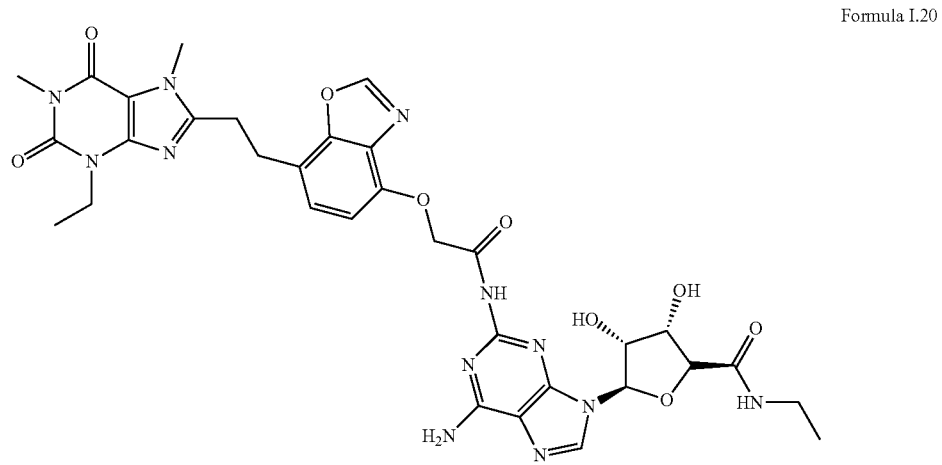

formula I.21,
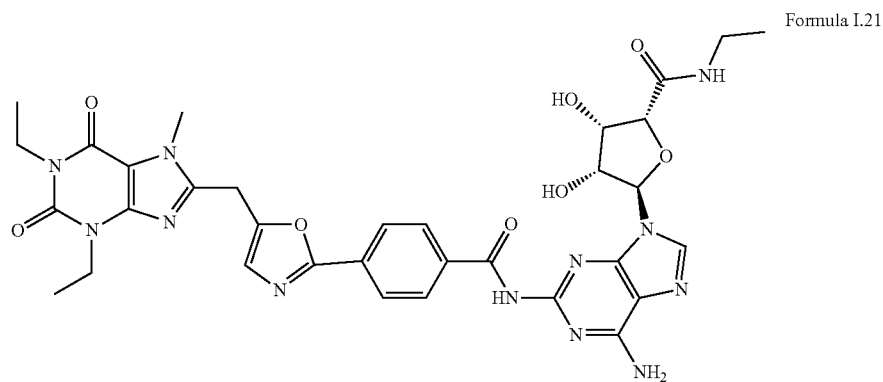 [SMILES: CCNC(=O)[C@@H]1O[C@@H](n2cnc3c(N)nc(NC(=O)c4ccc(-c5ncc(Cc6nc7c(c(=O)n(CC)c(=O)n7CC)n6C)o5)cc4)nc32)[C@H](O)[C@@H]1O]
formula I.22,
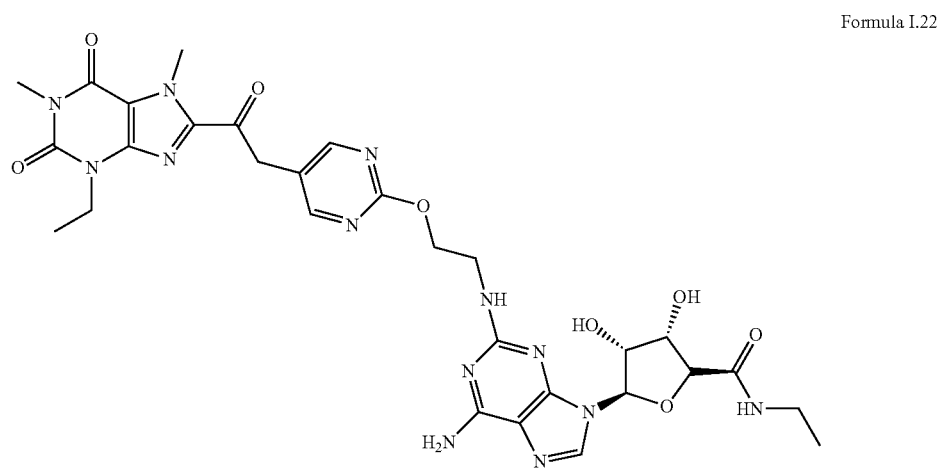
formula I.23, and
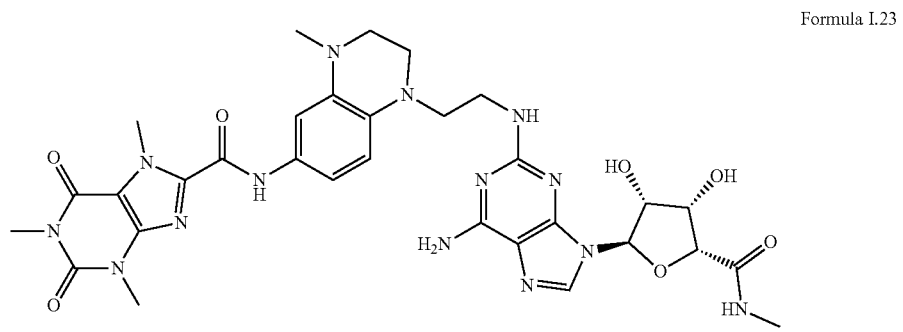

formula I.24.

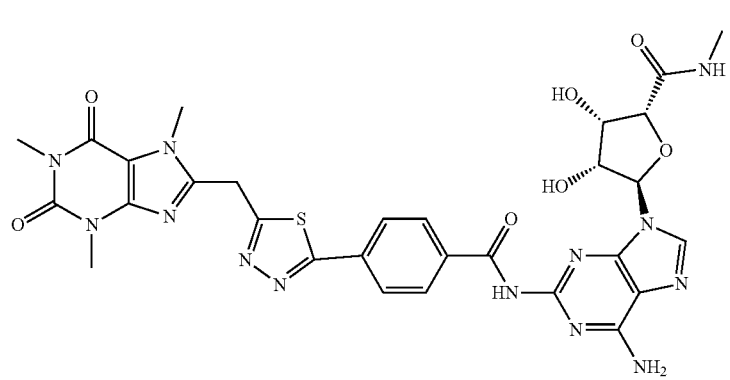

Formula I.24

4. A compound of formula I according to claim 1 for use as a medicament for the treatment of neurodegenerative diseases.

5. A compound according to claim 4, wherein the neurodegenerative disease is Parkinson's disease, Huntington's disease, Alzheimer's disease, amyotrophic lateral sclerosis (ALS), primary progressive aphasia, progressive supranuclear pulsatile diseases.

6. A compound according to claim 5, wherein the neurodegenerative disease is Parkinson's disease.

7. Pharmaceutical compositions comprising molecules of formula I according to claim 1.

8. A pharmaceutical composition according to claim 7, further comprising at least one other active ingredient in addition to the compounds represented by formula I.

9. A pharmaceutical composition according to claim 8, wherein the other active agent is selected from a group comprising acetylcholinesterase inhibitors, N-methyl-D-aspartate (NMDA) receptor antagonists, dopamine derivatives, dopamine agonists, anticholinergics, MAO-B inhibitors, COMT inhibitors, anticonvulsants, antipsychotics agents, antidepressants.

10. A pharmaceutical composition according to claim 7, comprising at least one excipient.

* * * * *